United States Patent
Liu et al.

(10) Patent No.: US 9,427,829 B2
(45) Date of Patent: Aug. 30, 2016

(54) DI- OR POLY-FUNCTIONAL ELECTRON DEFICIENT OLEFINS COATED METAL POWDERS FOR SOLDER PASTE

(71) Applicant: Henkel IP & Holding GmbH, Duesseldorf (DE)

(72) Inventors: Puwei Liu, San Marcos, CA (US); Barry N. Burns, Dublin (IE); Matthew J. Holloway, Naas (IE); Blake Olsen, Irvine, CA (US); Edward Ho, Garden Grove, CA (US); John Killoran, Dublin (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 341 days.

(21) Appl. No.: 14/199,179

(22) Filed: Mar. 6, 2014

(65) Prior Publication Data
US 2014/0182746 A1    Jul. 3, 2014

Related U.S. Application Data

(63) Continuation of application No. PCT/US2012/050138, filed on Aug. 9, 2012.

(60) Provisional application No. 61/531,475, filed on Sep. 6, 2011.

(51) Int. Cl.
| | |
|---|---|
| B23K 35/02 | (2006.01) |
| B23K 35/26 | (2006.01) |
| B23K 35/365 | (2006.01) |
| C07C 255/23 | (2006.01) |
| B22F 1/00 | (2006.01) |
| B23K 35/36 | (2006.01) |
| C08L 33/20 | (2006.01) |

(52) U.S. Cl.
CPC ......... *B23K 35/0244* (2013.01); *B22F 1/0062* (2013.01); *B23K 35/025* (2013.01); *B23K 35/0222* (2013.01); *B23K 35/262* (2013.01); *B23K 35/36* (2013.01); *B23K 35/365* (2013.01); *B23K 35/3613* (2013.01); *C07C 255/23* (2013.01); *C08L 33/20* (2013.01)

(58) Field of Classification Search
CPC .......................... B23K 35/0244; B22F 1/0062
USPC .................................................. 219/145.21
See application file for complete search history.

(56) References Cited

U.S. PATENT DOCUMENTS

| | | |
|---|---|---|
| 3,975,422 A | 8/1976 | Buck |
| 4,012,402 A | 3/1977 | Buck |
| 4,452,861 A | 6/1984 | Okamoto et al. |
| 4,607,091 A | 8/1986 | Schreiber |
| 4,994,326 A | 2/1991 | Shimmura et al. |
| 5,021,484 A | 6/1991 | Schreiber et al. |
| 5,180,752 A | 1/1993 | Melber et al. |
| 5,200,452 A | 4/1993 | Schreiber |
| 5,281,388 A | 1/1994 | Palmer et al. |
| 5,290,825 A | 3/1994 | Lazar |
| 5,315,462 A | 5/1994 | Ohkubo et al. |
| 5,328,522 A | 7/1994 | Sowa et al. |
| 5,369,192 A | 11/1994 | Ko et al. |
| 5,397,611 A | 3/1995 | Wong |
| 5,439,635 A | 8/1995 | Seemann |
| 5,445,911 A | 8/1995 | Russell et al. |
| 5,480,603 A | 1/1996 | Lopez et al. |
| 5,567,499 A | 10/1996 | Cundiff et al. |
| 5,580,656 A | 12/1996 | Melber |
| 5,677,048 A | 10/1997 | Pushaw |
| 5,736,074 A | 4/1998 | Hayes et al. |
| 5,851,336 A | 12/1998 | Cundiff et al. |
| 5,902,535 A | 5/1999 | Burgess et al. |
| 6,077,380 A | 6/2000 | Hayes et al. |
| 6,096,848 A | 8/2000 | Gololobov et al. |
| 6,156,146 A | 12/2000 | Cundiff |
| 6,207,786 B1 | 3/2001 | Ishida et al. |
| 6,294,629 B1 | 9/2001 | O'Dwyer et al. |
| 6,416,863 B1 | 7/2002 | Schulze et al. |
| 6,475,331 B1 | 11/2002 | O'Connor et al. |
| 7,368,167 B2 | 5/2008 | Johnston et al. |
| 2005/0171273 A1 | 8/2005 | Ledwidge et al. |
| 2007/0007692 A1 | 1/2007 | Lehmann et al. |

FOREIGN PATENT DOCUMENTS

| | | |
|---|---|---|
| CN | 1079929 A | 12/1993 |
| CN | 1478285 A | 2/2004 |
| JP | 02182809 A | 7/1990 |
| JP | H11302704 A | 11/1998 |
| JP | 2006506234 A | 2/2006 |
| JP | 2007095526 A | 4/2007 |
| JP | 2011046992 | 3/2011 |
| KR | 1020060100626 A | 9/2006 |
| WO | 8606738 A1 | 11/1986 |
| WO | 0185861 A1 | 11/2001 |
| WO | 2010059924 A2 | 5/2010 |
| WO | WO2010059924 A1 | 5/2010 |
| WO | 2010091975 A1 | 8/2010 |

OTHER PUBLICATIONS

S. Rimdusit and H. Ishida, "Development of new class of electronic packaging materials based on ternary system of benzoxazine, epoxy, and phenolic resin," Polymer, 41, 7941-49 (2000).
International Search Report for International Patent Application No. PCT/US09/065296 mailed on Jul. 1, 2010.

*Primary Examiner* — Weiping Zhu
(74) *Attorney, Agent, or Firm* — Steven C. Bauman

(57) ABSTRACT

The present invention relates to cured products of di- or poly-functional electron deficient olefins coated onto at least a portion of a surface of metal powders, such as metal powders used as appropriate in the formation of solder alloys, spheres and pastes.

16 Claims, 3 Drawing Sheets

DI- OR POLY-FUNCTIONAL ELECTRON DEFICIENT OLEFINS COATED METAL POWDERS FOR SOLDER PASTE

CROSS-REFERENCE TO RELATED APPLICATION

This application claims the benefit of U.S. Provisional Patent Application No. 61/531,475 filed Sep. 6, 2011, the contents of which are incorporated herein by reference.

BACKGROUND

1. Field

The present invention relates to cured products of di- or poly-functional electron deficient olefins coated onto at least a portion of a surface of metal powders, such as metal powders used as appropriate in the formation of solder alloys, spheres and pastes.

2. Brief Description of Related Technology

Solder is widely used in the assembly of semiconductor packages and semiconductor devices.

For instance, solder balls or spheres are used in the assembly of semiconductor packages, such as in flip chip applications. It is known to place a stearic acid coating on the surface of such solder balls or spheres.

Solder paste is commonly used for surface-mounted soldering of electrical components to circuit boards. Solder paste is useful because it can be applied to selected areas of the circuit board with its tackiness characteristic providing the capability of holding the electrical components in position without additional adhesives before forming the permanent bonds as the board passes through the solder reflow process.

Solder paste typically comprises a solder powder, a resinous component such as rosin, activators such as organic acids or amines, rheological control agents, thickeners and solvents. The solder paste is typically coated on the circuit board by techniques such as screen printing, dispensing, and transfer printing. Thereafter, the electrical components are placed on the circuit board and the solder paste is reflowed, by which the solder is heated sufficiently to cause it to melt and thereafter is cooling the solder sufficiently to cause it to solidify.

One problem in the industry associated with the use of solder paste is that it often has a short and unpredictable shelf life, e.g., typically from about one month to six months. The unpredictability in shelf life is caused, at least in part, by variations in the lag time from when the solder powder is made to the time it is mixed with flux to form solder paste, thereby resulting in variations in the degree of oxidation on the solder powder. Such oxidized powder does not reflow as well as unoxidized powder. Further, when the solder powder is combined with flux, which is inherently corrosive, the solder powder often reacts with the flux, thereby oxidizing the powder and reducing the acidity, thus effectiveness, of the flux. As a result, the performance of the solder paste often deteriorates over time. Moreover, the reaction between the solder powder and the flux typically causes the viscosity of the solder paste to increase substantially, which can make printing the solder paste difficult if not impossible depending on pitch.

Attempts have been made to reduce the reaction rate between the solder powder and the flux and thereby increase the shelf life of the solder paste, by storing the solder paste under refrigeration conditions. However, refrigeration is not effective to compensate for the varying degrees of oxidation on the solder powder prior to its incorporation into the solder paste.

It has also been reported that solder powder has been coated with materials that are non-reactive with the solder paste. For example, U.S. Pat. No. 4,994,326 discloses that coating agents that are insoluble or hardly soluble in a vehicle for solder pastes including those based on silicone and fluorine such as, for instance, silicone oils, silicone base high-molecular compounds, fluorinated silicone oils, fluorosilicone resins and fluorinated hydrocarbon base high-molecular compounds, are used as coatings.

The '326 patent also discloses a relatively large amount of coating material which is applied to the solder powder. While the relatively large amount of coating material may be effective to inhibit oxidation of the solder powder, in general, large amounts of coating material are undesirable since they can create a barrier which can inhibit the reflow of the solder. Moreover, such large amounts of coating material may cause physical obstructions and/or impurities which result in poor reflow characteristics, such as inadequate substrate wetting by the flux which can cause poor spreading of the solder and a discontinuous solder connection.

In addition, the '326 patent discloses the use of fluorinated hydrocarbons which are used as solvents in coating the solder powder. Currently, fluorinated hydrocarbons are considered to be an environmental pollutant and the use thereof is generally undesirable.

U.S. Pat. No. 6,416,863 is directed to and claims a method of encapsulating solder metal powder in which the powder is provided with a thin polymer protective layer by a polymerization reaction running on the surface of the solder powder, with the following steps:

a) producing a suspension of powder and a hydrophobic liquid, b) generating a hydrophobic surface layer on each metal particle by adding a cationic tenside with a chain length of $C_1$ through $C_{20}$ with continuous stirring to form a brush structure on the hydrophobic layer of step (a), c) stirring the mixture of steps a) and b) until formation of a viscous homogeneous mass, d) adding a radically polymerizable monomer to the mass of step c) and which forms a thermoplastic polymer with a glass temperature Tg of at least 60° C. below the solidus temperature of the solder powder, e) adding an organic initiator to start an interfacial polymerization reaction with incorporation of the hydrophobic layer of step b) and formation of a protective layer of thermoplastic polymer which has fluxing agent characteristics, f) introducing the mass of step e) into an aqueous preparation with continuous stirring, whereby the preparation contains an emulsifier for suspension stabilization and controlling the polymerization reaction by tempering to 50° C. to 90° C. and maintaining this temperature for at least 120 min, and g) cooling, washing and recovering the encapsulated solder powder of steps e) and f). Suitable monomers for forming the encapsulating wall are reported to be radically polymerizable monomers, preferably methacrylic-2-hydroxyethylester or methylmethacrylate.

U.S. Pat. No. 5,328,522 is directed to and claims a solder paste comprising (i) a flux and (ii) a coated solder powder comprising solder particles coated with parylene (having a melting point lower than the solder particles) in an amount from about 0.001 to about 0.5 weight percent based on the total weight of the coated solder powder and effective to inhibit oxidation of the solder particles in the solder paste without substantially inhibiting reflow characteristics of the coated solder powder.

U.S. Pat. No. 4,452,861 (Okamoto) describes solid particles encapsulated with cyanoacrylate polymer. The particles are encapsulated to prevent degradation due to reactive or corrosive surroundings. The cyanoacrylate polymer is used to coat phosphor particles and the like which are employed as coatings in cathode ray tubes and the like. Cerium activated calcium sulphide phosphor powder is the exemplified material which is coated.

U.S. Patent Application Publication No. 2005/0171273 describes a curable composition for forming anisotropically conductive bonds comprising:
(i) an amount of a first substantially uncured curable component; and
(ii) conductive particles coated with the cured product of a second curable component, where the coated-conductive particles are dispersed within the first curable component.

International Patent Publication No. WO 2010/059924 is directed to a metal particle having a thermally decomposable polymer coated on at least a portion of a surface thereof, where the thermally decomposable polymer has a ceiling temperature below a degradation temperature of the thermally decomposable polymer and below a melting point of the metal particles. Examples of the thermally decomposable polymer are disclosed as a cyanoacrylate polymer or a dicyclopentadiene polymer.

Despite the reported efforts documented above, there is a long felt need that remains unsolved regarding the provision onto a metal particle of a robust protective coating to minimize oxidization and thus improve storage stability of the metal particle before mixing into sensitive matrices, which are susceptible to contamination.

SUMMARY

That needs has now been solved. For instance, broadly speaking cured products of di- or poly-functional electron deficient olefins coated onto at least a portion of a surface of metal powders, such as metal powders used as appropriate in the formation of solder alloys, spheres and pastes, are provided herein.

The present invention is particularly useful in connection with zinc-containing metal alloys, such as tin-zinc alloys, since zinc is a very reactive metal having a thermally decomposable polymer formed from at least one di- or poly-functional electron deficient olefin coated on at least a portion of a surface thereof.

The present invention provides a metal particle having a thermally decomposable polymer formed from at least one di- or poly-functional electron deficient olefin coated on at least a portion of a surface thereof.

DETAILED DESCRIPTION

Figure 1:
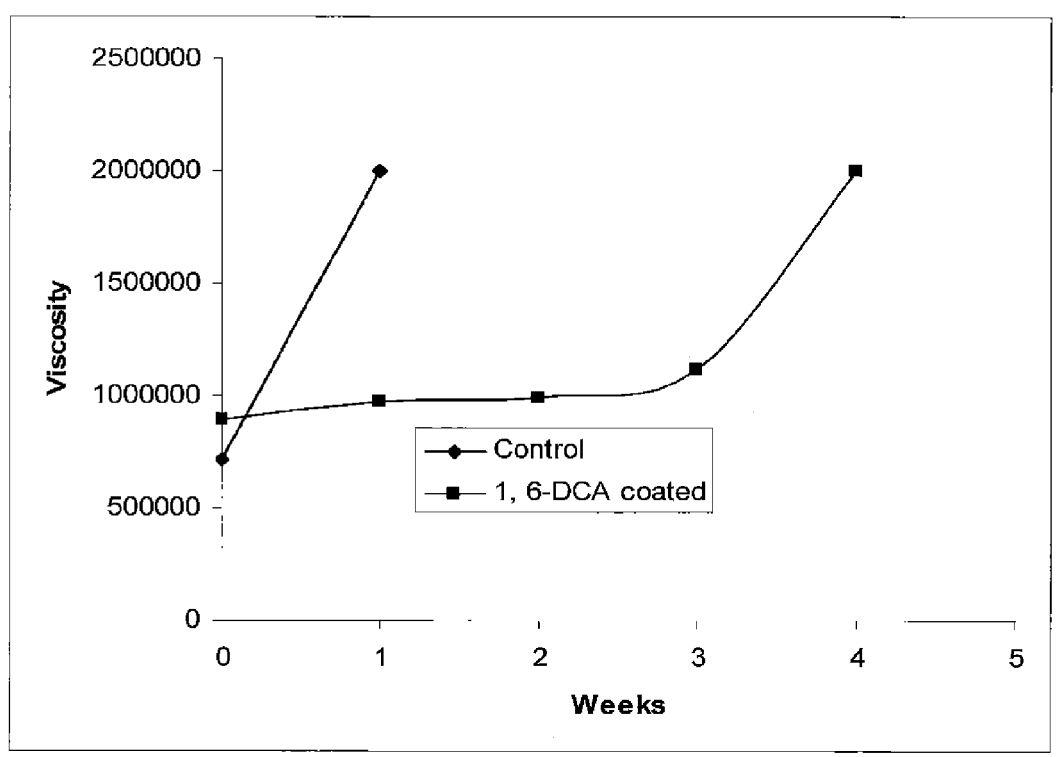
FIG. 1 depicts a plot of viscosity (measured in Mpas at 25° C.) over time (measured in weeks) of SnZn metal particles, uncoated as a control (depicted as the solid diamond) on the one hand and coated with 1,6-hexane diol bis-cyanoacrylate (depicted as a solid square) on the other, in a flux medium.

As noted above, the present invention provides a metal powder having a thermally decomposable polymer formed from at least one di- or poly-functional electron deficient olefin coated on at least a portion of a surface thereof. The coated metal powder is particularly suitable for use in solder pastes.

The cured product of the di- or poly-functional electron deficient olefin has as its chief function the task of physically isolating the metal particles from environmental degradation, such as oxidation and chemical reaction with flux media. In general the cured product acts as a physical barrier toward oxidation while the metal powder and/or solder paste in which the coated metal particle is being stored for use.

The di- or poly-functional electron deficient olefin is desirably a cyanoacrylate. Cyanoacrylates cure on exposure to metal particles, and thus from the vantage point of ease of cure are a desirable choice for a protectant. When the cyanoacrylate polymer decomposes, such as during exposure to processing temperatures, such as at the temperature reached during solder reflow, its remnants are simply cyanoacrylate monomers. Cyanoacrylate polymers have a ceiling temperature, above which the polymers revert to the monomers from which they were made. Most polymers, however, have a ceiling temperature that is higher than their degrading temperature. In practice therefore those polymers do not actually observe a ceiling for them. Other polymers, like cyanoacrylate polymers, have a very low ceiling temperature (oftentimes in the range of about 120 to about 150° C.).

In addition, cyanoacrylate monomers may be included together with the di- or poly-functional electron deficient olefins, when those olefins themselves are not cyanoacrylates or are not solely cyanoacrylates.

The di- or poly-functional electron deficient olefin may be represented by structure I:

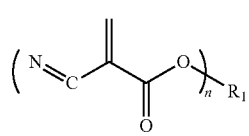

I where $R^1$ is selected from $C_{1-16}$ alkyl, alkoxyalkyl, cycloalkyl, alkenyl, alkynyl, arylalkyl, aryl, allyl and haloalkyl groups, and n is 2-4.

Desirably, the di- or poly-functional electron deficient olefin is a di-functional cyanoacrylate, though tri-functional or tetra-functional cyanoacrylates may be used as well.

Di-functional cyanoacrylates are embraced by structure II

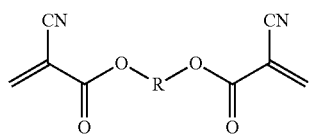

where R in structure II is a linkage selected from $(CH_2)_n$, with n being 2, 3, 4, 5, 6, 8, 9, 10, or 12, such as a linear or branched chain alkylene. Di-functional cyanoacrylates of this sort may be prepared through a trans-esterification reaction using an appropriate diol to yield the alkylene center segment for "R". Desirable examples of these di-functional cyanoacrylates include 1,5-pentanediol bis-cyanoacrylate, 1,6-hexanediol bis-cyanoacrylate, 1,8-octanediol bis-cyanoacrylate, 1,9-nonanediol bis-cyanoacrylate, 1,10-decanediol and 1,12-dodecanediol bis-cyanoacrylate, with1,10-decanediol bis-cyanoacrylate, 1,8-octanediol bis-cyanoacrylate, and 1,6-hexane bis-cyanoacrylate being particularly desirable. An appropriate synthetic method to yield such di-functional or bis-cyanoacrylates may be found generally in U.S. Pat. No. 3,975,422 (Buck), U.S. Pat. No. 4,012,402 (Buck), and U.S. Pat. No. 6,096,848 (Gololobov), and International Patent Publication No. WO 2010/091975.

Suitable cyanoacrylate monomers for use together with di- or poly-functional electron deficient olefin are alkyl, alkenyl and alkoxy cyanoacrylate esters, more particularly where the alkyl or alkenyl group of such esters has up to 10 carbon atoms. Reference to structure I, where n is 1 provides a visual depiction of such monomers. The cyanoacrylate monomer may be selected from methyl, ethyl, n-propyl, iso-propyl, n-butyl, iso-butyl, sec-butyl, tert-butyl, n-pentyl, iso-pentyl, n-hexyl, iso-hexyl, n-heptyl, iso-heptyl, n-octyl, n-nonyl, allyl, methoxyethyl, ethoxyethyl, 3-methoxybutyl and methoxyisopropyl cyanoacrylate esters.

Cure accelerators may be employed with the cyanoacrylate, in the event that a metal particle which is to be coated is somewhat slow to react with the cyanoacrylate. These include the accelerators disclosed in International Patent Application Publication No. WO 01/85861, hereby incorporated in its entirety by reference. Other examples of cure accelerators suitable for use here include U.S. Pat. No. 6,475,331 (Grismala) and U.S. Pat. No. 6,294,629 (O'Dwyer), both of which are hereby incorporated in their entirety by reference.

In certain applications the metal particles will be placed between two substrates, for example between two conductive substrates such as in a semiconductor package application. In this way the particle should be sufficiently uncoated to form a conductive pathway between the substrates it bridges. In such circumstances the bringing together of the substrates may be sufficient to "flatten" (deform by pressing upon) the metal particle and break sufficiently whatever coating was on the surface of the particle.

The metal particles may be mono-sized, i.e., substantially of the same dimensions. This may be important if the bond gap formed is a semiconductor package or assembly, for instance is desirably of a particular size. However, particles of varying dimensions can be used, so as to have a relatively wide distribution of diameters about a mean value such as from about 0.5 to about 100 µm in at least one dimension, desirably about 3 to about 50 µm. In particular, it is desirable that the coated particles are spherical in shape.

Desirably the coating on the particles is less than about 3 µm, more particularly in the range from about 0.001 to about 0.2 µm, such as from 0.004 to about 0.4 µm, for example from about 0.01 to about 0.1 µm. The coating on the particles can also be determined as a function of weight gain on the particles after the coating process is completed.

The cured product coated on the metal particles lends to the stability of the metal particles, and of formulations in which the coated metal particles are used, by mitigating against the reactivity of the particles towards environmental contaminates or in the case of a formulation, such as solder paste, other components that are used to form the formulation. In the latter case, viscosity increases over time would indicate poor stability because the metal particles are reacting with formulation constituents.

In the context of a solder reflow process, after application of the solder paste, cured product coated on the metal particles is at least partially removed by exposure to the elevated temperatures reached during reflow so as to expose the surface of the metal particle, i.e., here, the solder powder. The polymer coating may also be at least partially removed by physical breaking (for example by applying sufficient pressure to the particle to deform it to cause breaking of the coating). The cured product coated metal particles may be employed in many applications. One of cured product application is in the electronics industry generally and in particular in solder paste, such as is in flip-chip applications, and solder sphere application. In solder paste applications, for instance, the coated metal particles are present in amount of from about 5 to about 98% by weight with respect to the total component.

The cured product coated metal particles and formulations, such as solder pastes, which are made therewith, and solder spheres are particularly useful for establishing electrical interconnections between semiconductor chips and substrates.

Any type/shape of the metal particle may be used. In particular the particles may be spherical or tending toward spherical. Suitable metals of the metal particle include elemental metals such as tin, silver, copper, lead, zinc, indium, bismuth, and rare earth metals. In addition, alloys such as tin/silver/copper, tin/bismuth, tin/lead, tin/zinc and tin/indium/bismuth, may also be the basis of the metal particle.

In some cases, the di- or poly-deficient electron deficient olefin may have a vapour pressure that allows for a vapour deposition thereof onto the metal particles. There, by exposing the metal particles to the vapour of the cyanoacrylate component, a uniform coating of polymerised cyanoacrylate can be formed on the surface of the particles. Vapor deposition allows for uniform coatings to be applied to the particles. For example, the particles may be exposed to any suitable vapor arising at ambient temperature, or the temperature may be suitably raised to create the vapor. In the case of cyanoacrylates, the contact of the vapor with the surface of the particle may be sufficient to polymerize the reactive monomer. A fluidized bed reactor may be employed for the preparation of the coated metal particles. A vapor of the reactive monomer may be injected into the fluid bed of the reactor.

The invention also relates to a method of forming a polymer coating on a metal particle which includes the steps of:

a) providing a plurality of metal particles;
b) applying to the plurality of metal particles a di- or poly-functional electron deficient olefin under suitable conditions so as to substantially coat at least a portion of the surface of most of the metal particles; and c) exposing the di- or poly-functional electron deficient olefin-coated metal particles to suitable conditions to form a cured product thereof on the surface of the metal particle.

The invention also relates to a method of forming solder paste which includes the steps of:

a) providing a di- or poly-functional electron deficient olefin as a coating on at least a portion on the surface of solder powder;

b) providing two or more of solder paste components selected from rosin, activators, rheological control agents, thickeners, or solvents; and c) blending the di- or poly-functional electron deficient olefin coated solder powder with the solder paste components to form a solder paste.

A more hydrophobic layer on the surface of the metal powder yields better protection against environmental contaminants when stored and premature reaction where formulated in a solder paste, for instance.

The invention will be described now with reference to the following non-limiting Example(s).

EXAMPLES

Example 1

Synthesis

Initially, a series of bis-cyanoacrylates are synthesized, consistent with the procedure set forth at page 14 of International Patent Publication No. WO 2010/091975. Those bis-cyanoacrylates are: 1,6-hexanediol bis-cyanoacrylate, 1,8-octanediol bis-cyanoacrylate and 1,10-decanediol bis-cyanoacrylate.

Example 2

Cyanoacrylate Coating Process

The cyanoacrylate coating process was designed to exclude any external catalysts so that polymerization will be initiated by the metal surface itself so that the cyanoacrylate polymer to be formed grows on the metal surface.

500 g of SnZn solder powder (Sn 91%, Zn 9%) (average size of 30 um, type 3, Sn91Zn9, and supplied by IPS) was placed into a 2 L size round bottom flask along with 1 L of anhydrous toluene. To the SnZn solder powder was added 0.2 g of 1,6 hexane diol bis-cyanoacrylate, and the flask was placed on a rotary evaporator, rotating at 100 rpm to allow uniform mixing. After a period of time of about 1 hour, the mixture was filtered to remove the solvent and the powder was rinsed twice with fresh toluene to remove any residual cyanoacrylate polymer that did not form directly on the solder powder. The coated solder powder was allowed to dry in room temperature.

Example 3

Solder paste formulations were prepared from a solder flux referred to as LF320 which comprises Rosin (CAS No. 8050-09-7/EINECS No. 232-475-7) in an amount of 1-33%, Modified rosin (CAS No. 144413-22-9) in an amount of 1-33% and Neodecanoic acid (CAS No. 26896-20-8/EINECS No. 248-093-9) in an amount of 1-33%, into which was mixed the SnZn metal particles at a level of 12% by weight.

Example 4

Viscosity Test/Brookfield Viscosity

Brookfield viscometers employ the principle of rotational viscometry. That is, viscosity is measured by sensing the torque required to rotate a T bar spindle at constant speed while immersed in the sample. The torque is proportional to the viscous drag on the immersed spindle, and thus to the viscosity of the paste. The test is carried out at specific temperature on solder paste that has been prepared in a prescribed manner.

Place sample at 25° C. for 6 hours.

After 6 hours, remove sample from 25° C., open and remove internal plunger. Scrape any paste adhering to plunger and add to sample.

Using spatula, stir paste gently for 30 seconds taking care to avoid the introduction of air.

Use Brookfield viscometer RVDV-II+ on helipath stand with TF spindle attached. Set rotation speed to 5 rpm.

Set bottom of helipath travel 40 mm below surface of paste. Set spindle 3 mm below surface of paste.

Start spindle rotation and helipath stand descent.

Record viscosity at lowest point of descent.

Referring to Table 1 below, SnZn solder powder coated with 1,6-hexane diol bis-cyanoacrylate and mixed into a LF320 flux medium at a level of 12% by weight showed favourable viscosity as measured in $10^6$ cPs build up over time at a temperature of 25° C. tested by the Brookfield method as compared with the control. The so-called SnZn solder powder was able to withstand nearly 4 weeks of the viscosity test environment, without demonstrating adverse effects, whereas the control could not withstand 1 week under that environment. This data is demonstrated graphically with reference to FIG. 1.

TABLE 1

| Time (Weeks) | 0 | 1 | 2 | 3 | 4 |
|---|---|---|---|---|---|
| Uncoated SnZn control | 0.7 | >2.0 | | | |
| 1,6-Hex Diol CA coated ZnSn | 0.8 | 0.9 | 1.0 | 1.2 | >2.0 |

Viscosity Test/Parallel Plate Viscosity

Viscosity using the so-called parallel plate method was determined on a StressTech Reologica Instruments AB Rheometer. Here, SnZn solder powder coated with 1,6-hexane diol bis-cyanoacrylate and mixed into a LF320 flux medium at a level of 12% was used to form solder paste formulations. The so-formed solder paste was pressed between two parallel plates at a fixed gap of 1 mm. A constant shear rate of 1 rpm and 5 rpm was applied to one plate and the viscosity was estimated from the angular force required to maintain this shear rate.

The test is carried in a prescribed manner, as follows.

Samples are used at room temperature.

Attach 40 mm parallel plate to rheometer and zero gap. Set gap to 1 mm for testing.

Place enough sample on bottom plate so it covers full volume between plates when pressed down to 1 mm.

Run test method, as described above

Plot of observed Viscosity (y axis) vs. Time (x axis)

Referring to Table 2 below, SnZn solder powder coated with 1,6-hexane diol bis-cyanoacrylate and mixed into a LF320 flux medium at a level of 12% showed favourable viscosity as measured in $10^6$ cPs build up over time at a temperature of 40° C. tested by the parallel plate method as compared with the control. The so-called SnZn solder power was able to withstand 28 days of the viscosity test environment without demonstrating adverse effects whereas the control was not. This data is demonstrated graphically FIG. 2.

TABLE 2

| Time (Days) | Initial | 4 | 5 | 6 | 7 | 11 | 12 | 13 | 14 | 18 | 21 | 28 |
|---|---|---|---|---|---|---|---|---|---|---|---|---|
| Uncoated SnZn control | 0.8 | 2.2 | | | | | | | | | | |
| 1,6-Hex Diol CA coated ZnSn | 0.8 | 1.2 | 1.5 | 1.4 | 1.2 | 1.2 | 1.4 | 1.5 | 1.4 | 1.5 | 1.5 | 1.8 |

Figure 2:
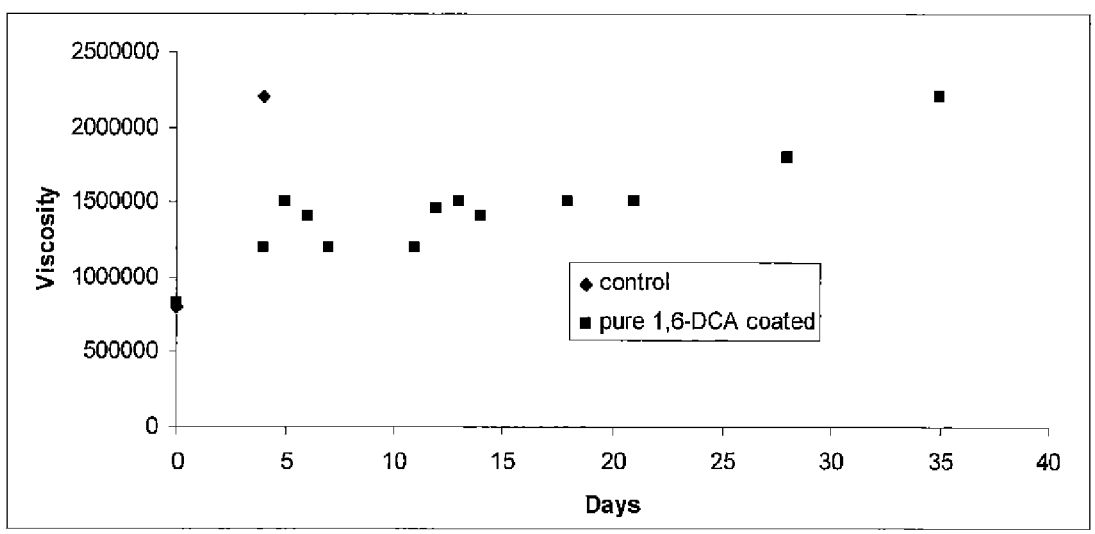
FIG. 2 depicts a plot of viscosity (measured in Mpas at 40° C.) over time (measured in days) of SnZn metal particles, uncoated as a control (depicted as the solid diamond) on the one hand and coated with 1,6-hexane diol bis-cyanoacrylate (depicted as a solid square) on the other, in a flux medium.

Reference to FIGS. 1 and 2 shows the remarkable improvement of viscosity maintenance in a flux medium for SnZn-coated metal particles with a bis-cyanoacrylate compared to the uncoated metal particles.

Figure 3:
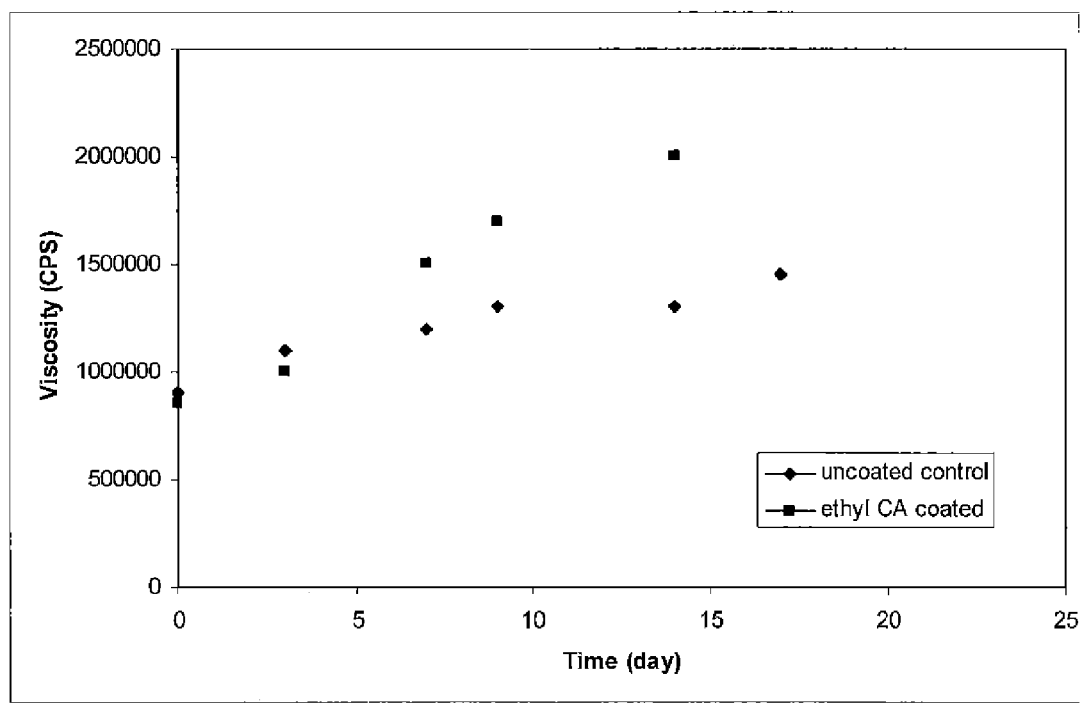
FIG. 3 depicts a plot of viscosity (measured in Mpas at 25° C.) over time (measured in days) of SnZn metal particles, uncoated (depicted as the solid diamond) on the one hand and coated with ethyl cyanoacrylate (depicted as a solid square) on the other, in a flux medium.

Referring to Table 3, below, SnZn solder powder coated with ethyl cyanoacrylate and mixed into a LF320 flux medium at a level of 12% should unfavourable viscosity as measured in 106 cPs buildup overtime at a temperature of 25° C. tested by the parallel plate method as compared with the central reference to FIG. 3 shows the lack of viscosity maintenance demonstrated by an ethyl cyanoacrylate-coated SnZn metal particle, where it performed somewhat less satisfactorily in that flux medium on this metal particle than the uncoated metal particle.

TABLE 3

| Time (Days) | Initial | 3 | 7 | 9 | 14 | 17 |
|---|---|---|---|---|---|---|
| Uncoated SnZn | 0.90 | 1.10 | 1.20 | 1.30 | 1.30 | 1.45 |
| Ethyl cyanoacrylate coated SnZn | 0.85 | 1.00 | 1.50 | 1.70 | >2.00 | |

Referring to Table 4 below, SnAgCu solder powder coated with octyl cyanoacrylate showed favourable viscosity build up over time as compared with the control, and was able to withstand 5 weeks of the viscosity test without failing whereas the control was not.

TABLE 4

| | Time (Weeks)/Viscosity (CPs) | | | | |
|---|---|---|---|---|---|
| Sample | Initial | 2 weeks | 3 weeks | 4 weeks | 5 weeks |
| Control | 1174000 | 1700000 | 1822000 | 1598000 | off scale |
| CA Coated Sample | 1164000 | 1566000 | 1516000 | 1418000 | 1542000 |

While mono-functional alkyl cyanoacrylate-coated metal particles perform better with respect to viscosity maintenance in solder paste formulations than uncoated metal particles in Type 4 solder powder (Tin, Cu and Ag alloy), for Type 3 solder powder (Tin and Zinc alloy) the reverse is observed.

What is claimed is:

1. A metal particle having di- or poly-functional electron deficient olefin coated on at least a portion of a surface thereof, wherein the di- or poly-functional electron deficient olefin is embraced by the following structure

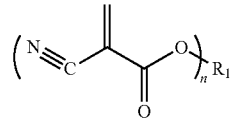

wherein $R^1$ is $C_1$-$C_{40}$ alkyl, $C_2$-$C_{40}$ alkenyl, or $C_3$-$C_{40}$ cycloalkyl group, with hydroxyl or alkoxy functionality and/or ether linkages being optional, and n is 2-4.

2. A metal particle according to claim 1 wherein the di- or poly-functional electron deficient olefin has a ceiling temperature below or equal to a melting point of the metal particle.

3. A metal particle according to claim 1 wherein the di- or poly-functional electron deficient olefin further comprises cyanoacrylate monomers embraced by the following structure:

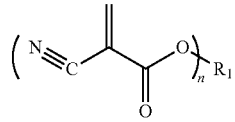

wherein $R^1$ is $C_1$-$C_{40}$ alkyl, $C_2$-$C_{40}$ alkenyl, or $C_3$-$C_{40}$ cycloalkyl group, with hydroxyl or alkoxy functionality and/or ether linkages being optional, and n is 1.

4. A metal particle according to claim 1 wherein the cyanoacrylate is selected from the group consisting of 1,5-pentanediol bis-cyanoacrylate, 1,6-hexanediol bis-cyanoacrylate, 1,8-octanediol bis-cyanoacrylate, 1,9-nonanediol bis-cyanoacrylate, 1,10-decanediol bis-cyanoacrylate and 1,12-dodecanediol bis-cyanoacrylate.

5. A metal particle according to claim 1 wherein the metal particle is solder.

6. A metal particle according to claim 1 wherein the metal particle is made from elemental metals.

7. A metal particle according to claim 1 wherein the metal particle is made from an alloy.

8. A metal particle according to claim 1 wherein the metal particle is made from an elemental metal selected from the group consisting of tin, silver, copper, lead, zinc, indium, bismuth, and rare earth metals.

9. A metal particle according to claim 1 wherein the metal particle is made from an alloy selected from the group consisting of tin/silver/copper, tin/bismuth, tin/lead, tin/zinc and tin/indium/bismuth alloys.

10. A metal particle according to claim 1 wherein the polymer coating on the metal particle is less than about 5 µm in thickness.

11. A metal particle according to claim 1 wherein the polymer coating on the metal particle is in the range from about 0.0001 to about 3.0 µm in thickness.

12. A metal particle according to claim 1 wherein the polymer coating on the metal particle is in the range from about from 0.001 to about 1 µm in thickness.

13. A solder paste composition comprising the coated metal particle according to claim 1.

14. A solder paste composition claim 13 wherein the coated metal particles are present in amount of from about 5 to about 98% by weight with respect to the total component.

15. A method of forming a polymer coated metal particle according to claim 1 which includes the steps of:
 a) providing a plurality of metal particles;
 b) applying a di- or poly-functional electron deficient olefin to substantially coat at least a portion of the surface of the metal particles; and
 c) permitting di- or poly-functional electron deficient olefin to cure as a polymer coating on the metal particles.

16. A method of forming a solder paste composition according to claim 13 which includes the steps of:
 a) providing solder powder comprising the coated metal particle;
 b) providing solder paste components; and
 c) blending the polymer coated solder powder with the solder paste components to form a solder paste.

* * * * *